United States Patent [19]

Gyure et al.

[11] Patent Number: 5,665,075

[45] Date of Patent: Sep. 9, 1997

[54] METHOD OF MAKING A NEEDLE SHIELD ASSEMBLY

[75] Inventors: Sandor Gyure, West Orange, N.J.; Tracy R. Hottovy, Columbus, Nebr.; Alex S. Wallace, Mahwah, N.J.; Jay E. Booth, Canaan, Conn.; Bronwen Walters, Dania, Fla.

[73] Assignee: Becton, Dickinson and Company, Franklin Lakes, N.J.

[21] Appl. No.: 675,752

[22] Filed: Jul. 3, 1996

[51] Int. Cl.[6] .................................................. A61M 5/00
[52] U.S. Cl. ........................................ 604/263; 604/192
[58] Field of Search .............................. 604/263, 187, 604/110, 192, 199; 128/919; 206/365, 366, 364

[56] References Cited

U.S. PATENT DOCUMENTS

| | | | |
|---|---|---|---|
| 3,658,061 | 4/1972 | Hall | 128/214.4 |
| 4,664,259 | 5/1987 | Landis | 206/365 |
| 4,867,746 | 9/1989 | Dufresne | 604/192 |
| 4,872,552 | 10/1989 | Unger | 206/365 |
| 4,883,469 | 11/1989 | Glazier | 604/192 |
| 4,886,503 | 12/1989 | Miller | 604/192 |
| 4,909,791 | 3/1990 | Norelli | 604/192 |
| 4,909,792 | 3/1990 | Norelli | 604/192 |
| 4,944,397 | 7/1990 | Miller | 206/365 |
| 4,944,731 | 7/1990 | Cole | 604/192 |
| 4,950,249 | 8/1990 | Jagger et al. | 604/192 |
| 4,976,699 | 12/1990 | Gold | 604/192 |
| 4,982,842 | 1/1991 | Hollister | 206/365 |
| 5,011,475 | 4/1991 | Olson | 604/192 |
| 5,116,325 | 5/1992 | Paterson | 604/192 |
| 5,135,509 | 8/1992 | Olliffe | 604/192 |
| 5,139,489 | 8/1992 | Hollister | 604/192 |
| 5,151,089 | 9/1992 | Kirk, III et al. | 604/192 |
| 5,188,611 | 2/1993 | Orgain | 604/192 |
| 5,207,653 | 5/1993 | Janjua et al. | 604/192 |
| 5,232,454 | 8/1993 | Hollister | 604/192 |
| 5,232,455 | 8/1993 | Hollister | 604/192 |
| 5,242,417 | 9/1993 | Paudler | 604/192 |
| 5,312,369 | 5/1994 | Arcusin et al. | 604/192 |
| 5,405,332 | 4/1995 | Opalek | 604/192 |

*Primary Examiner*—John D. Yasko
*Attorney, Agent, or Firm*—John L. Voellmicke

[57] ABSTRACT

A needle shield assembly having a single-use cannula lock of the present invention includes a needle cannula having a proximal end, a distal end and a lumen therethrough. A hub includes a proximal end for connection to a fluid transfer device and a distal end connected to the proximal end of the needle cannula. A collar is rotationally connected to the hub so that the collar can be rotated around the hub. An elongate needle cover removably engages the hub and covers the needle cannula. An elongate needle shield having a proximal end and a distal end is hingedly connected, through its proximal end, to the collar. The needle shield includes two sidewalls defining a longitudinal opening and a back wall between said side walls defining a recess having an interior surface. The needle shield is capable of pivoting from an open position wherein the needle cannula is exposed, to a closed needle protecting position wherein at least part of the needle cannula is within the longitudinal opening of the needle shield. The needle shield assembly further includes structure for preventing the needle shield from pivoting into the closed position unless the needle cover is removed, and structure for locking the needle shield in the closed needle protecting position when the needle shield is pivoted into the closed position. The structure for locking traps the needle cannula in the longitudinal opening of the needle shield.

7 Claims, 11 Drawing Sheets

METHOD OF MAKING A NEEDLE SHIELD ASSEMBLY

FIELD OF THE INVENTION

The subject invention relates to needle shields for hypodermic needles, to help prevent accidental contact with the needle.

Background

Accidental needle sticks with a used hypodermic needle can transmit disease. Most prior art needle assemblies have a needle shield. Some needle shields define a rigid sleeve that can be telescoped distally over the needle cannula. This procedure requires a healthcare worker to hold the needle assembly or the associated medical implement in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of disposing or shielding at a more convenient time. However, until the needle is shielded or properly disposed, the device presents a potential danger to other people.

A needle shield which is hinged near the base of the needle has the advantage of allowing one-handed needle reshielding, thus providing the opportunity for reshielding, under most circumstances, immediately after use.

A hinged needle shield which permanently locks when it is pivoted to the closed needle shielding position has certain advantages. Primarily, there is no doubt about the status of the needle shield assembly and the healthcare worker knows that the needle should be carefully disposed of and not used for further fluid transfer. This is analogous to the prior art rigid cylindrical needle shield which is telescoped over the needle cannula and frictionally engages the needle hub. It is clear with the prior art needle assembly whether the needle is shielded or not shielded. However, having a permanently lockable hinged needle shield presents a problem in situations where the needle is intended to be used twice. For example, the needle is first used to penetrate the pierceable stopper of a medication vial for the purpose of filing the syringe with medication for subsequent injection into a patient. The needle shield assembly with attached syringe is then transported to the patient area for injection of the medication. If the needle is re-shielded permanently after the syringe is filled it cannot be used for injection and a second needle must be installed at the time of use.

It is advantageous to have a self-contained needle shield assembly wherein the adapter for the medical implement, the needle cannula, and the needle shield are all connected in one unit. The prior art includes syringes having cylindrical sleeves over their outside diameter. After injection, the sleeve is advanced to a locked needle protecting position. The syringes are important safety devices, however, not all syringes are used with a needle. The use of a self-contained needle shield assembly allows the end user to attach the needle assembly onto a variety of syringe sizes and to inventory standard syringes for all uses. Accordingly, a more costly safety syringe would not have to be used for applications where the safety features are not necessary.

It is also advantageous to have an enclosed needle cover that protects the cleanliness of the needle even after the needle shield assembly is removed from its sterile package. An enclosed needle cover protects all sides of the needle while a hinged needle shield has one open side and allows exposure of the needle to airborne particles.

Although the prior art provides many improved needle shield devices, there is still a need for a self-contained needle shield assembly wherein the needle shield can be positioned in the needle shielding position using a one-handed procedure and the needle shield automatically locks in the needle shielding position and is unable to be reused. There is a need for a self-contained needle shield assembly which allows the needle to be used twice, once for withdrawing medication into a syringe and then for injecting the medication into a patient wherein the needle may be shielded between the first and second use. There is a need for a needle shield assembly which protects the cleanliness of the needle after the needle shield assembly is removed from its sterile package. There is also a need for a needle shield assembly that provides the shortest possible fluid path between the syringe barrel and the needle tip to avoid loss of medication in the fluid path which cannot be expelled.

SUMMARY OF THE INVENTION

A needle shield assembly having a single-use cannula lock of the present invention includes a needle cannula having a proximal end, a distal end and a lumen therethrough. A hub includes a proximal end for connection to a fluid transfer device and a distal end connected to the proximal end of the needle cannula. A collar is rotationally connected to the hub so that the collar can be rotated around the hub. An elongate needle cover removably engages the hub and covers the needle cannula. An elongate needle shield having a proximal end and a distal end is hingedly connected, through its proximal end, to the collar. The needle shield includes two sidewalls defining a longitudinal opening and a back wail between said side walls defining a recess having an interior surface. The needle shield is capable of pivoting from an open position wherein the needle cannula is exposed, to a closed needle protecting position wherein the needle cannula is within the longitudinal opening of the needle shield. The needle shield assembly further includes structure for preventing the needle shield from pivoting into the closed position unless the needle cover is removed, and structure for locking the needle shield in the closed needle protecting position when the needle shield is pivoted into the closed position. The structure for locking traps the needle cannula in the longitudinal opening of the needle shield.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention and not intended to limit the scope of the invention to those embodiments illustrated. The scope of the invention will be measured by the appended claims and their equivalents.

Adverting to FIGS. 1–8, a needle shield assembly having a single-use cannula lock, such as needle shield assembly 20, includes a needle cannula 21 having a proximal end 22, a distal end 23 and a lumen therethrough defining a longitudinal axis 25. In this preferred embodiment, the distal end of the needle cannula includes sharpened tip 26. It is within the purview of the present invention to include blunt cannula which are cannula without sharp tips. Blunt cannula are known in the art and are usually used to inject liquid into an I.V. set or other fluid path having an access port with a pre-slit septum. The blunt cannula is forced through the slit in the septum and into fluid communication with the fluid flow path. Upon removal of the blunt cannula, the slit portion of the septum automatically seals itself.

Figure 3:
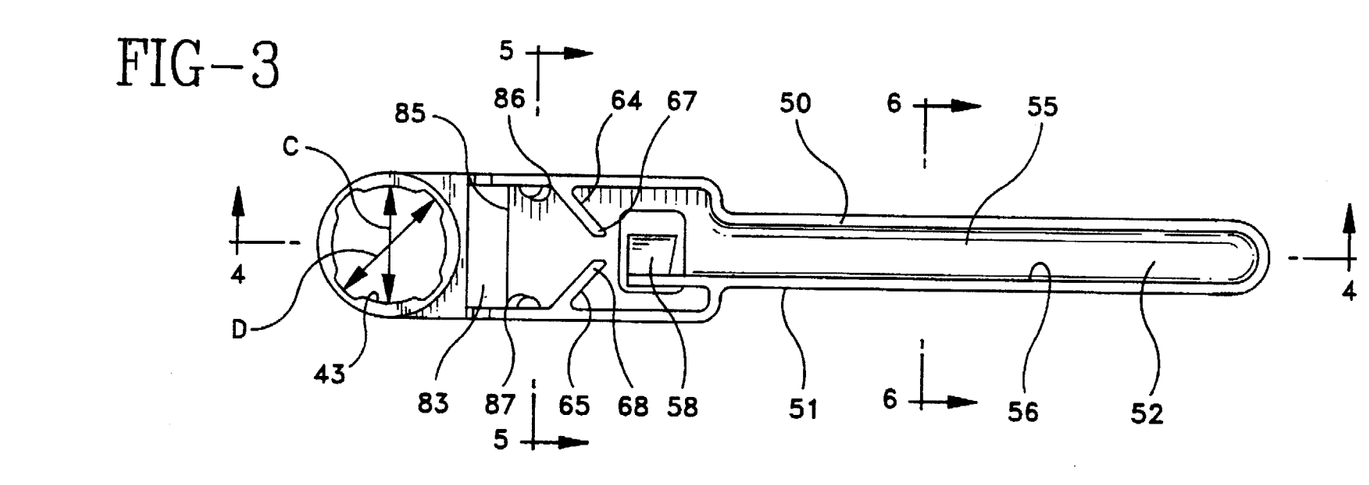
FIG. 3 is a top plan view of a needle shield and collar assembly for use in the present invention.

A hub 28 includes a proximal end 29 and a distal end 31 connected to proximal end 22 of the needle cannula. The hub includes a base member 30 which for the purposes of describing the instant invention is part of the hub. There are many ways of connecting the base member to the hub, such as through interference fit, adhesives, ultrasonic welding and the like. It is within the purview of the present invention to include a hub and its base member which are of a unitary one-piece structure. The one-piece structure may be accomplished by many methods including injection molding the hub and base member as a one-piece unit thereby eliminating the need to assemble the base member to the hub during the manufacturing process. In this preferred embodiment, the collar is rotatably connected to the hub in a snap-fit arrangement which allows the collar, through application of manual force, to be rotated around the hub. The rotational connection of the collar and hub is accomplished by interaction between structure on the hub including proximal raised portion 32, distal raised portion 33 and collar receiving recess 34 and the collar. The distance across proximal raised portion 32 and distal raised portion 33 is greater than the inside diameter of collar 41 and greater than the diameter or distance across recess 34. During assembly, the collar is passed over the distal end of the hub and forced over distal raised portion 33 so that it snaps into the space between raised portion 32 and raised portion 33 and is trapped in that position. It is preferred that there be a certain amount of frictional engagement between the collar and the hub so that the collar cannot rotate too freely with respect to the hub. As will be explained in more detail hereinafter it is desirable to be able to rotate the needle shield with respect to the needle hub and have the shield maintain itself in the selected position. This can be accomplished in many ways, such as, by making the distance between raised portion 32 and raised portion 33 less than the thickness of collar 41 and/or making the diameter or distance across recess 34 slightly larger than the inside diameter of the collar to provide a frictional relationship between the collar and the hub. Also mechanical retention can be provided by placing a series of projections on the hub or inside the collar and a series of recesses inside the collar or on the hub. The projections can engage the recesses to position the collar with respect to the hub but still allow rotation by overcoming the force of the projection and recess engagement. Interior surface 43 of collar 41 can be formed in a variety of shapes such as a constant inside diameter. In this preferred embodiment, interior surface 43 is defined by four segments along minor diameter C and four segments along major diameter D, as best illustrated in FIG. 3. Minor diameter C is slightly smaller than the diameter of recess 34 on hub 28. This stepped configuration makes the collar less sensitive to manufacturing tolerances so that the frictional fit between the collar and the hub can be more tightly controlled. The stepped configuration also gives the collar some flexibility to allow it to be easily snapped into place during the assembly process. The advantages of rotationally connecting the collar to the hub will be explained in more detail hereinafter.

Figure 2:
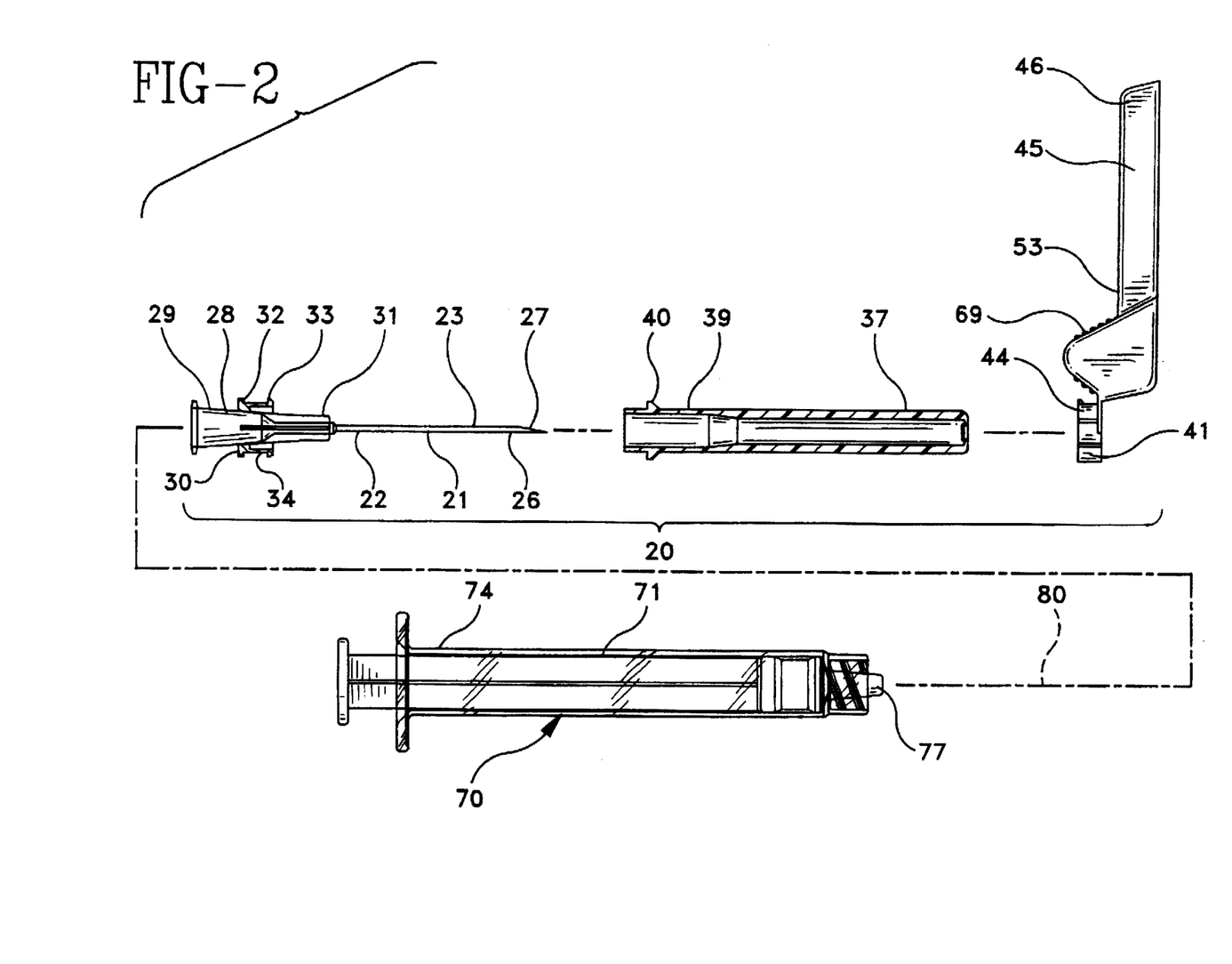
FIG. 2 is an exploded view illustrating the needle shield assembly of the present invention attached to a syringe with the needle cover and portions of the hub illustrated in cross-section.
Figure 7:
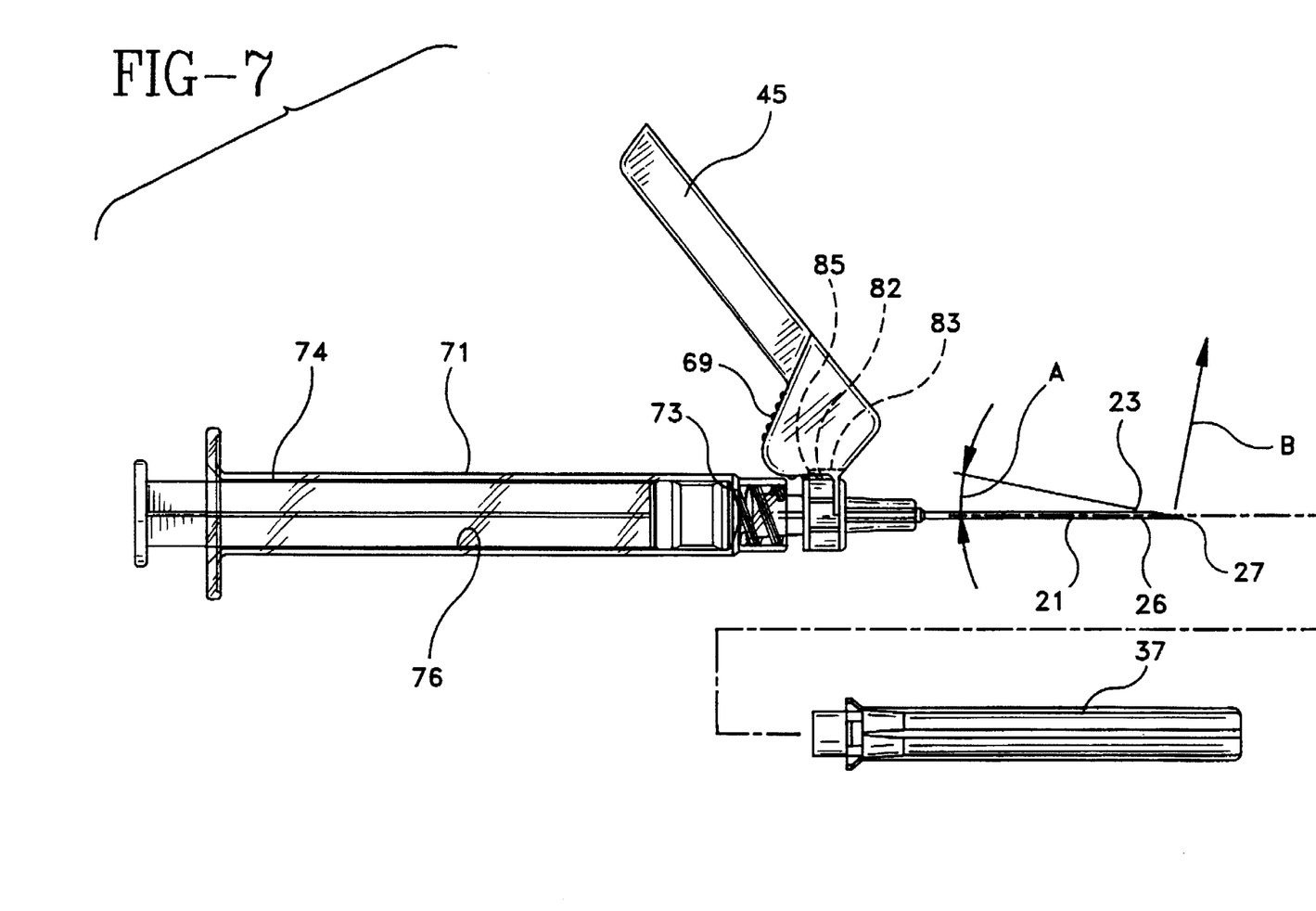
FIG. 7 is a side elevation view of the needle shield assembly of the present invention attached to a syringe at the time of first use.

An elongate rigid needle cover 37 having a cylindrically-shaped side wall 38 and an open proximal end 39 removably engages hub 28 and covers needle cannula 21, as best illustrated in FIG. 2. A needle cover is an important advantage of the present invention. Preferably, the needle assembly is manufactured and sterilized in a protective package with the needle cover in place. The needle cover provides a contamination barrier for the needle after the needle shield assembly is removed from the sterile package. Accordingly, the user is assured of a clean needle at the time of first use. At the time of first use, the needle cover is removed, as illustrated in FIG. 7, by overcoming engagement forces between the needle hub and the open proximal end of the needle cover.

An elongate needle shield 45 having a distal end 46 and a proximal end 47 is hingedly connected to collar 41. In this preferred embodiment, needle shield 45 is hingedly connected to collar 41 through living hinge 44. It is within the purview of the present invention to include any structure for hingedly connecting the shield to the collar so that the needle shield may be pivoted with respect to the collar. These structures include known mechanical hinges and various linkages, or combinations of hinges and linkages. Needle shield 45 includes two side walls 50 and 51 defining a longitudinal opening 52 and a back wall 53 between the side walls defining a recess 55 having an interior surface 56.

The needle shield assembly of the present invention is suitable for use with fluid delivery devices such as syringes. For the purpose of illustration, needle shield assembly 20 is illustrated connected to hypodermic syringe 70 comprising a syringe barrel 71 having a distal end 73, a proximal end 74 and a circular side wall 75 defining a chamber 76 for retaining fluid and a longitudinal axis 80. Volume measuring indicia 72 are on the barrel for measuring the dose of medication to be delivered. The distal end of the syringe barrel is connected to the hub so that the lumen of the needle cannula is in fluid communication with chamber 76 of the syringe barrel. In this embodiment, distal end 73 of the syringe barrel includes a frusto-conically shaped tip 77 having a passageway therethrough which provides a fluid path between the cannula and the chamber. The frusto-conically shaped tip of the syringe barrel frictionally engages a frusto-conically shaped cavity in the needle hub. The distal end of the syringe barrel also includes a locking luer-type collar 79 concentrically surrounding the tip. The luer collar has an internal thread which engages the needle hub to hold it securely to the barrel. It is within the scope of the present invention to include various hub configurations to attach to a wide variety of medical or other fluid handling devices. The hub configuration described hereinabove, having a frusto-conically shaped interior cavity, reflects one of these many possibilities. Many syringes, fluid handling devices, such as stopcocks and adapters, and other fluid handling devices contain luer slip and locking luer-type fittings to which the hub of a frusto-conically shaped interior cavity will properly engage. It is also within the purview of the present invention to provide a needle shield assembly wherein the hub is integrally molded with the syringe barrel.

It is an important feature of the present invention that all elements of the needle shield assembly are connected to the hub and that the hub is capable of directly connecting to a fluid handling device such as a syringe. Some prior art devices contain a separate housing which mounts between the needle hub and the syringe, wherein the needle shield is hingedly connected to the separate housing. A separate housing lengthens the fluid flow path between the chamber in the syringe and the distal end of the needle cannula thereby wasting medication, because it cannot be expelled, the fluid flow path through the housing must be filled with medication before medication can leave the proximal end of the needle. In some cases, the medication may cost one hundred times more than the syringe and small amounts of medication lost over a substantial number of syringes can result in a substantial unnecessary loss of valuable medication. Also, the additional element increases the length between the syringe and the needle tip possibly making it slightly more difficult to accurately position the needle, for example in a patient's vein.

The use of a needle cover and a hinged needle shield in the needle shield assembly of the present invention provides other advantages in the manufacturing and assembling of the needle shield assembly. Most notably, the needle cannula, hub and needle cover can be manufactured as a separate assembly. So long as the needle cover is attached to the hub the needle cannula and in particular the sharpened tip of the needle cannula is protected from damage and contamination. The final assembly step involves slipping collar 41 over needle cover 37 until the collar snaps into place on the collar receiving recess 34 of the hub. To facilitate this assembly, needle cover 37 includes annular flange 40 which has a tapered outside surface to allow the collar to pass smoothly over annular flange 40 and distal raised portion 33 of the hub and into recess 34 during assembly. Further, this final assembly step is accomplished while the fragile needle cannula is protected by needle cover 37, thus avoiding contamination and damage to the needle cannula.

Figure 8:
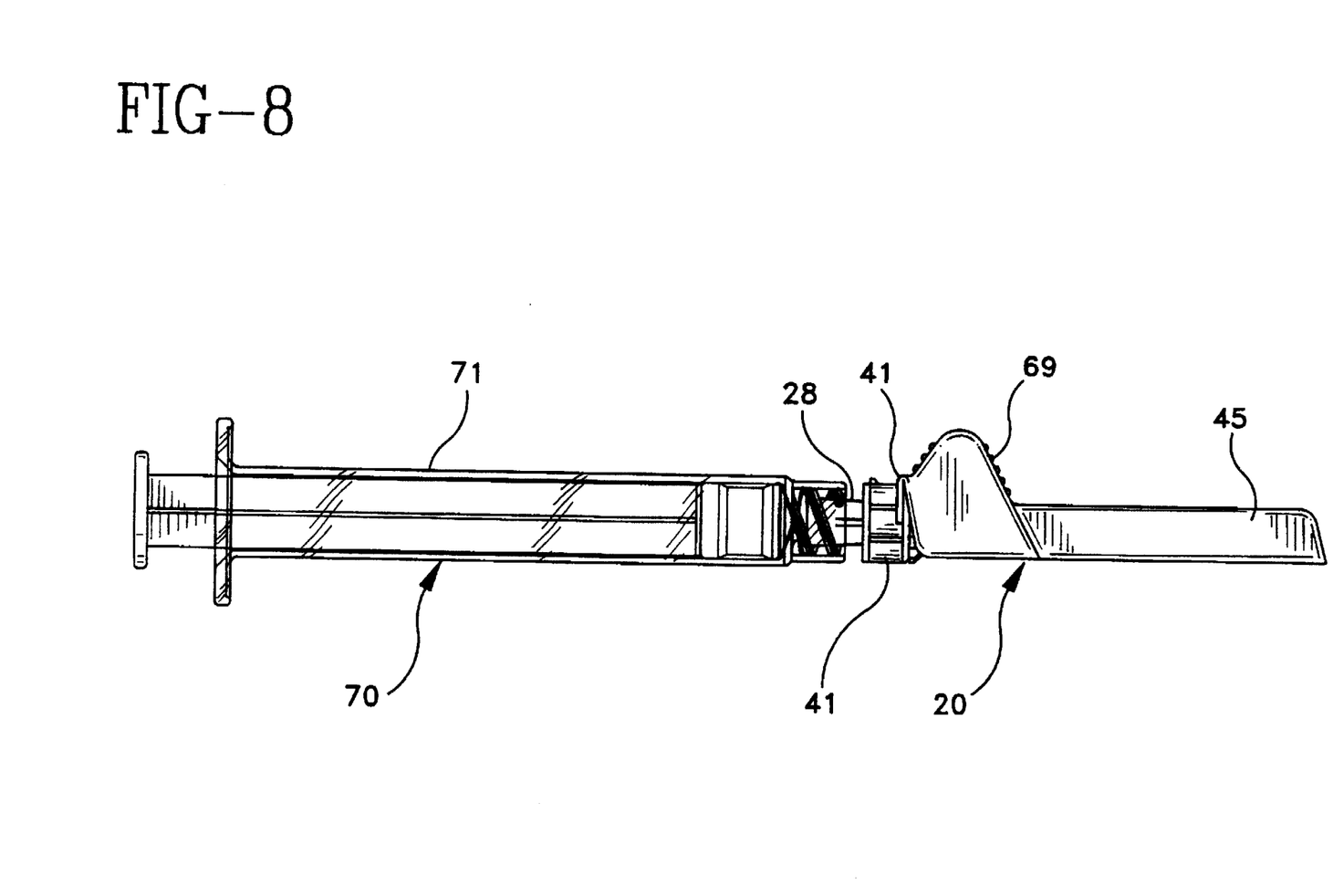
FIG. 8 is a side elevation view of the needle shield assembly of the present invention after use with the needle shield in the closed position.

Needle shield 45 is capable of pivoting from an open position wherein needle cannula 21 is exposed, as best illustrated in FIG. 7, to a closed needle protecting position wherein at least part of needle cannula is within the longitudinal opening of the needle shield, as best illustrated in FIG. 8.

As will be explained in more detail hereinafter, an important feature of the present invention includes means for preventing the needle shield from being pivoted into the closed position before the needle cover is removed. In this preferred embodiment means for preventing is accomplished forming at least a portion of the side walls so that the longitudinal opening is smaller than the needle cover, so that the needle cover must be removed before the needle shield can be pivoted into the closed needle protecting position. It is within the scope of the present invention to include many structures which prevent the movement of the needle shield into the closed needle protecting position before the needle cover is removed. Such structures may include a projection on the needle shield, the needle cover or on both elements which creates an interference between the needle shield and the needle cover which prevents moving the needle shield into the closed needle protecting position.

Another important feature of the present invention includes means for automatically locking the needle shield in the closed needle protecting position when the needle shield is pivoted into the closed position. "Automatically" is intended to mean that movement of the needle shield sufficiently into the needle protecting position will cause locking to occur automatically without further action on behalf of the user. "Permanently" is intended to mean that there is no unlocking structure, and the needle will remain shielded until proper disposal. The lock should generally withstand the normal forces encountered during proper disposal of the needle shield assembly. Excessive forces applied to the needle shield will bend the needle cannula but not allow the needle cannula to be re-exposed.

In this preferred embodiment, means for locking the needle shield in the closed needle protecting position includes needle cannula locking means for trapping the needle cannula in the longitudinal opening of the needle shield. In this preferred embodiment needle cannula locking means includes an arm 58 projecting from interior surface 56 of the needle shield. Arm 58 includes a transverse portion 61 at its free end 59. Transverse portion 61 includes a ledge 62 which is positioned so that when the needle shield is pivoted to the closed position, needle cannula 21 snaps past transverse portion 61 and is trapped in the needle shield by ledge 62. The action of the needle cannula snapping past the transverse portion can be accomplished by deflection of the arm and/or the transverse portion, by deflection of the needle cannula or by a combination of all elements so that after the needle cannula passes the transverse portion, the parts return generally to their undeflected position or at least to a position where the needle cannula cannot reverse its path and remains trapped in the recess of the needle shield. The retention forces are preferably such that an attempt to return the needle shield to the open needle exposing position will cause the needle to be bent in that direction but usually not re-exposed. In this preferred embodiment arm 58 extends from interior surface 56, and in particular outwardly from back wall 53. However, the arm could also extend from either of the side walls and still achieve a similar result.

Figure 5:
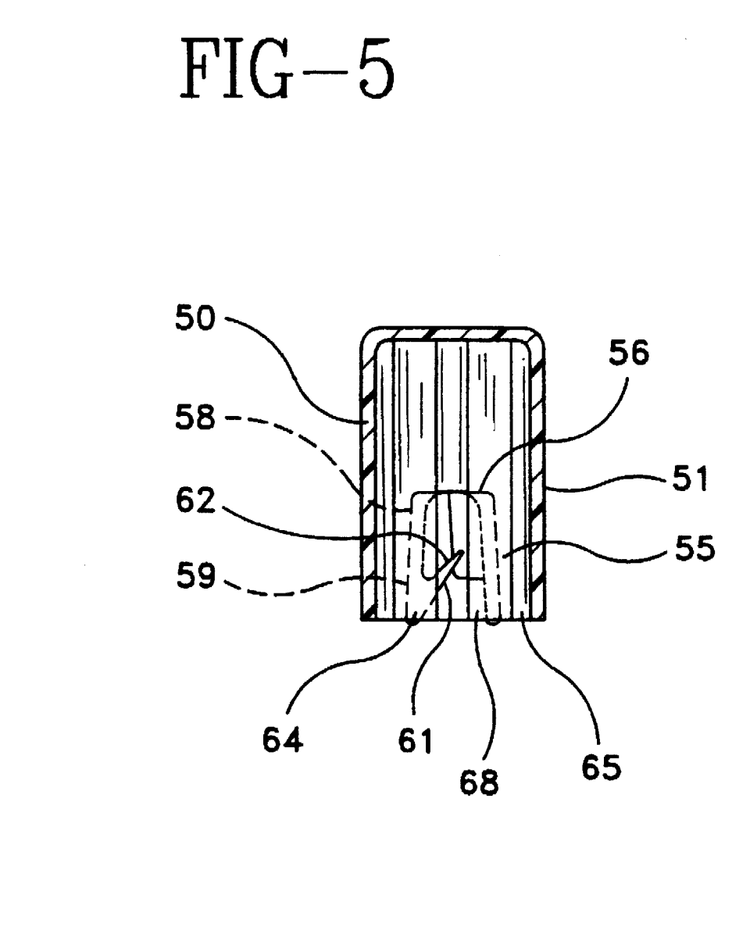
FIG. 5 is a cross-sectional view of the needle shield and collar assembly of FIG. 3 taken along lines 5—5.
Figure 6:
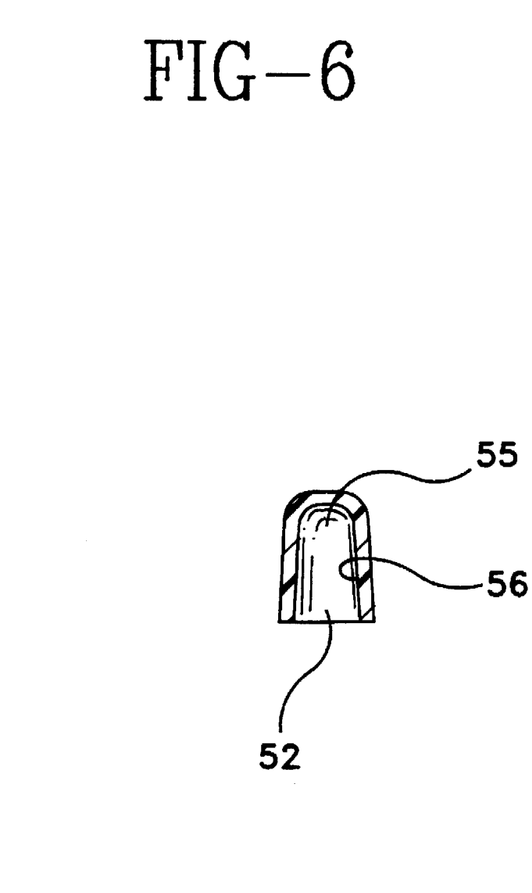
FIG. 6 is a cross-sectional view of the needle shield and collar assembly of FIG. 3 taken along lines 6—6.

In this preferred embodiment needle cannula locking means also includes first inclined wall 64 and second inclined wall 65 having exterior surfaces 67 and 68 respectively for urging the needle cannula toward the center of longitudinal opening 52 as the needle shield is being rotated into the closed position. The inclined walls are especially helpful if the longitudinal axis of the needle cannula is misaligned with respect to the longitudinal axis of the hub and syringe. The exterior surfaces will urge the needle cannula toward a central position so that it properly engages and is trapped by the arm structure. Although the inclined walls are not necessary for the present invention at least one wall is desirable and two walls, as best illustrated in FIGS. 3 and 5, are preferred.

Referring to FIGS. 7 and 8 it can be seen that the needle shield can be moved from the open position to the closed position using a single-handed procedure. For example, by grasping syringe 70 with the fingers and advancing the needle shield from the open to the closed position by pressing on the back wall with the thumb until the needle shield is in the closed locked position. To facilitate the single-handed operation of the needle shield, finger pad 69 is provided at the proximal end of the needle shield.

Figure 4:
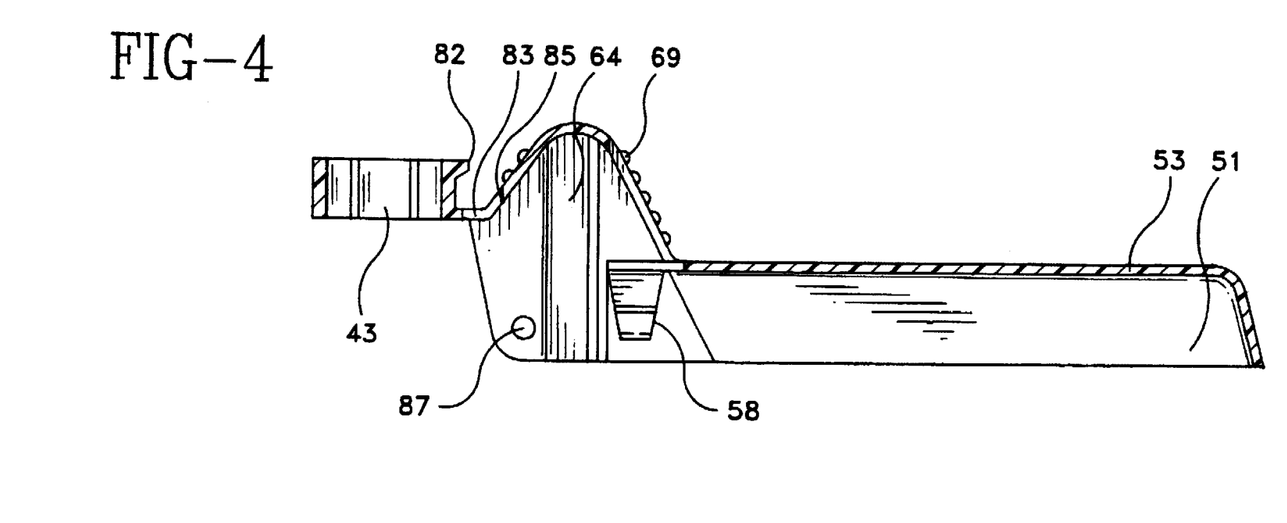
FIG. 4 is a cross-sectional view of the needle shield and collar assembly of FIG. 3 taken along lines 4—4.

It is desirable to have means for releasably retaining the needle shield in the open position. Holding the needle shield in the open position keeps it from interfering with the injection process either visually or physically. Releasably retaining the needle shield in the open position may be accomplished by dimensioning parts of the assembly so that friction is created in the hinge or by using an articulated over-center hinge or by creating some interference between the needle shield and the collar which must be forcefully overcome to move the needle shield out of the open position. In this embodiment, as best illustrated in FIG. 4, projection 82 on the collar will engage edge 85 of aperture 83 when the needle shield is pivoted to the open position. Additional force is required to pivot the needle shield out of the open position. In the open position, it is preferred that longitudinal opening 52 be oriented from between about 90° to 180° from longitudinal axis 25 of the needle cannula, as best illustrated in FIG. 7, where the needle shield is rotated so that longitudinal opening 52 is about 150° from longitudinal axis 25 of the needle cannula.

As best illustrated in FIG. 7, sharpened tip 26 of needle cannula 21 is sharpened to a bevel shape having a bevel surface 27 oriented at angle A with respect to longitudinal axis 25. Bevel surface 27 faces direction B. The rotational connection of the collar to the hub is an important feature of the present invention because it allows rotation of the needle shield so that the bevel surface faces the same side of the collar as the needle shield when the needle shield is in the open position. Rotation of the needle shield to this position optimally orients the bevel surface and makes it easier to insert the needle into a patient's vein or subcutaneously. Also, it is desirable to have bevel surface 27 facing the same side of the needle assembly as the needle shield when the needle shield is in the open position, so that the needle shield does not interfere with positioning the syringe at a low angle close to the patient's body, for example, the patient's arm, when attempting to gain access into a vein. In addition, the ability to rotate the needle shield with respect to the hub allows the needle shield to be positioned to avoid blocking the user's view of volume measuring indicia on the syringe barrel.

Figure 1:
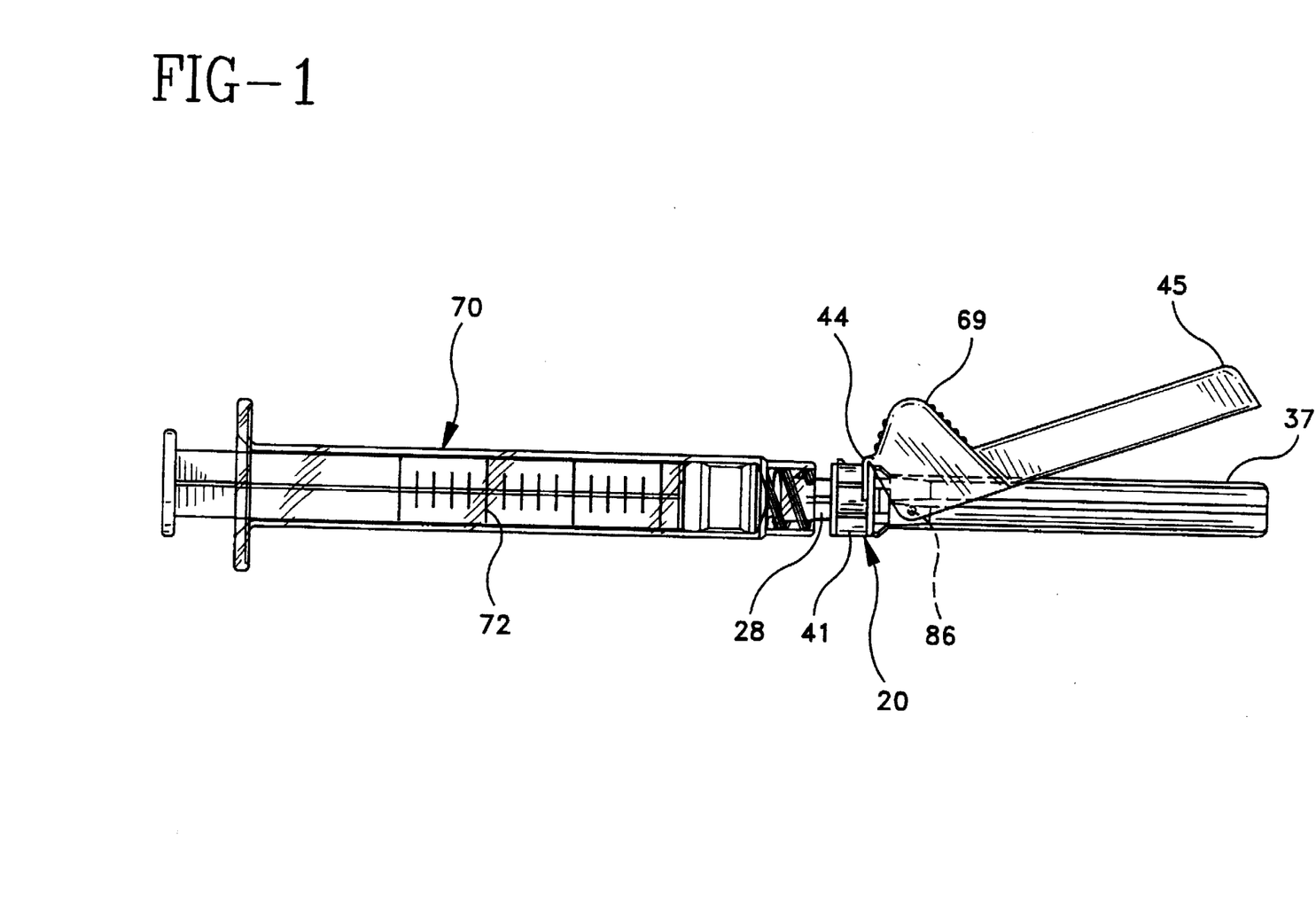
FIG. 1 is a side elevation view of the needle shield assembly of the present invention attached to a syringe before being used.

FIG. 1 illustrates needle shield assembly 20 connected to hypodermic syringe 70 in a configuration in which it is likely to be delivered, in sterile form, from a manufacturer. Placing needle shield 45 in an intermediate position between the closed position and the open position, closer to the closed position, creates a configuration which takes up less packaging and shipping carton space. This is especially true when the needle shield assembly is being shipped separately without being attached to a fluid delivery instrument such as a syringe. Also, in this intermediate position, the needle shield assembly is easier to handle for the purposes of installing it onto a fluid delivery device, such as screwing the hub onto a standard locking luer-type fitting. Accordingly, it is desirable to provide means for releasably retaining the needle shield in an intermediate position between the open position and the closed position. In this preferred embodiment means for releasably retaining the needle shield in the intermediate position includes protrusions 86 and 87 projecting inwardly from side walls 50 and 51 respectively engage the outer surface of needle cover 37 to bias the needle shield toward the needle cover. An additional force is required to pivotably move the needle shield from the intermediate position to the open position.

Figure 9:
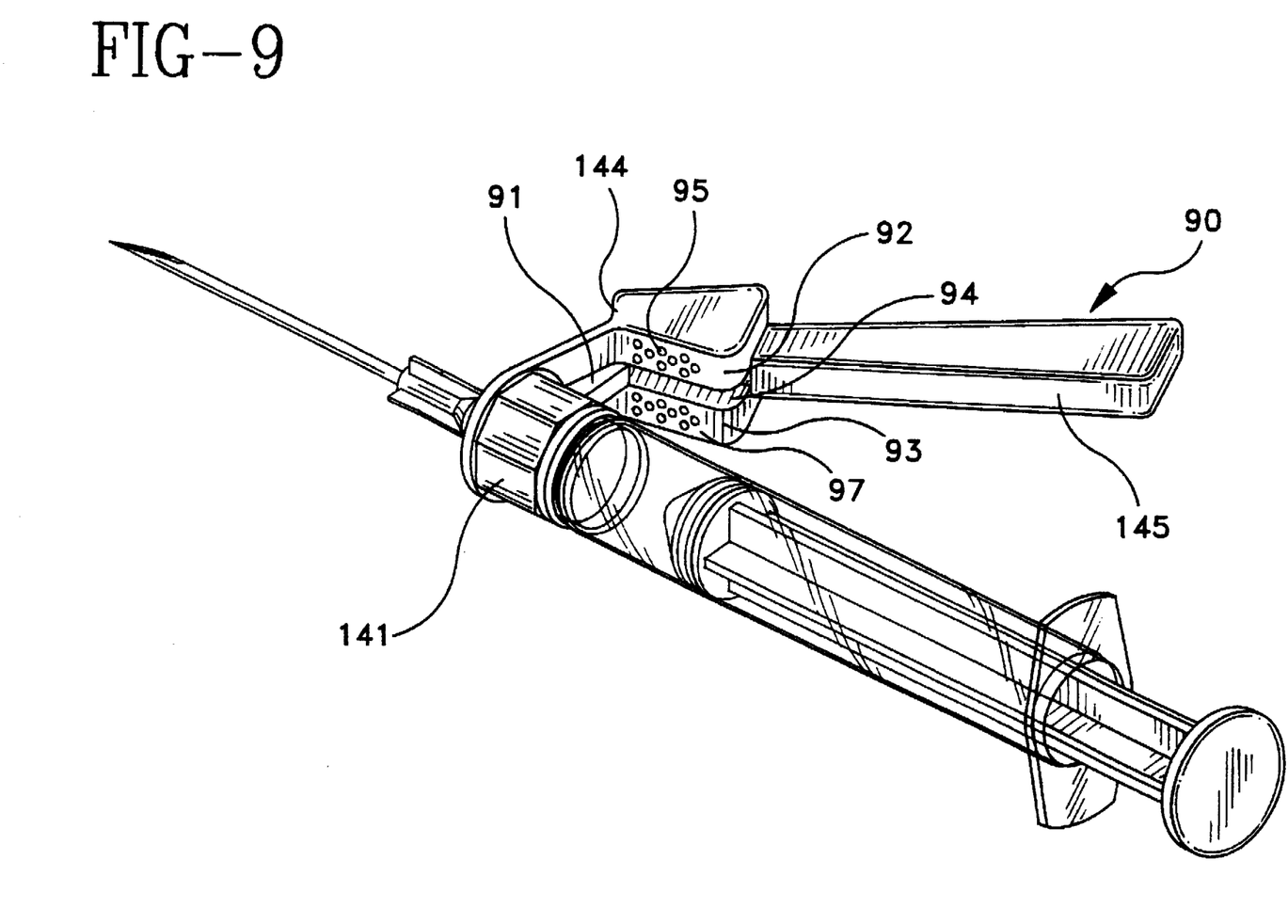
FIG. 9 is a perspective view of an alternative needle shield assembly of the present invention attached to a syringe.

FIG. 9 illustrates an alternative needle shield assembly of the present invention. The alternative needle shield assembly functions similarly to the needle shield assembly of FIGS. 1–8. Alternative needle shield assembly 90 includes collar 141 and a needle shield 145 hingedly connected to the collar through hinge 144. Means for releasably retaining the needle shield in the open position includes a projection 91 on the collar and finger pads 92 and 93, on the needle shield, defining slot 94 therebetween. The width of slot 94 between finger pads 92 and 93 is preferably equal to or slightly less than the width of projection 91 on the collar so that when the needle shield is pivoted to the open position projection 91 enters slot 94 and is frictionally engaged therein by the sides of finger pads 92 and 93. Projections or recesses can be provided alternatively on projection 91 and in slot 94 to provide for a mechanical engagement of the needle shield to the collar when the needle shield is in the open position. In any case, the needle shield is releasably retained in this position and additional force will be needed to overcome the frictional or mechanical engagement of the projection to the needle shield to advance the needle shield to the closed position. Discontinuous surfaces 95 and 97 are provided to help to provide a more positive connection between the user's finger and the needle shield when advancing the needle shield to the closed position.

Figure 10:
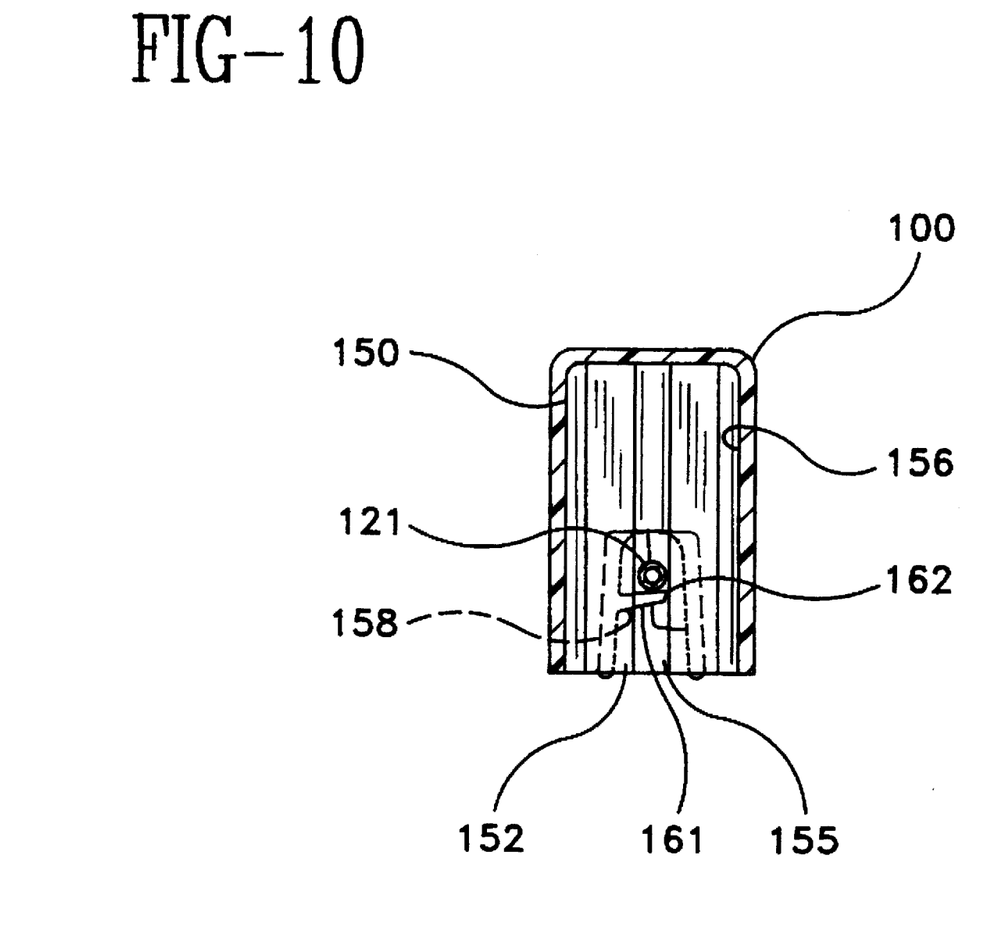
FIG. 10 is a cross-sectional view of an alternative needle shield.

FIG. 10 illustrates an alternative needle shield for use with the needle shield assembly of the present invention. The alternative needle shield of the embodiment of FIG. 10 functions similarly to the needle shield assembly of FIGS. 1–8.

Alternative needle shield 100 includes side walls 150 and 151 defining a longitudinal opening 152 and a back wall between the side walls defining a recess 155 having an interior surface 156. Needle cannula locking means for trapping the needle cannula in the longitudinal opening of the needle shield includes an arm 158 having a transverse portion 161 at its free end including a ledge 162 positioned so that when the needle shield is pivoted to the closed position, the needle cannula 121 snaps past transverse portion 161 and is trapped in the needle shield by a ledge 162.

Figure 11:
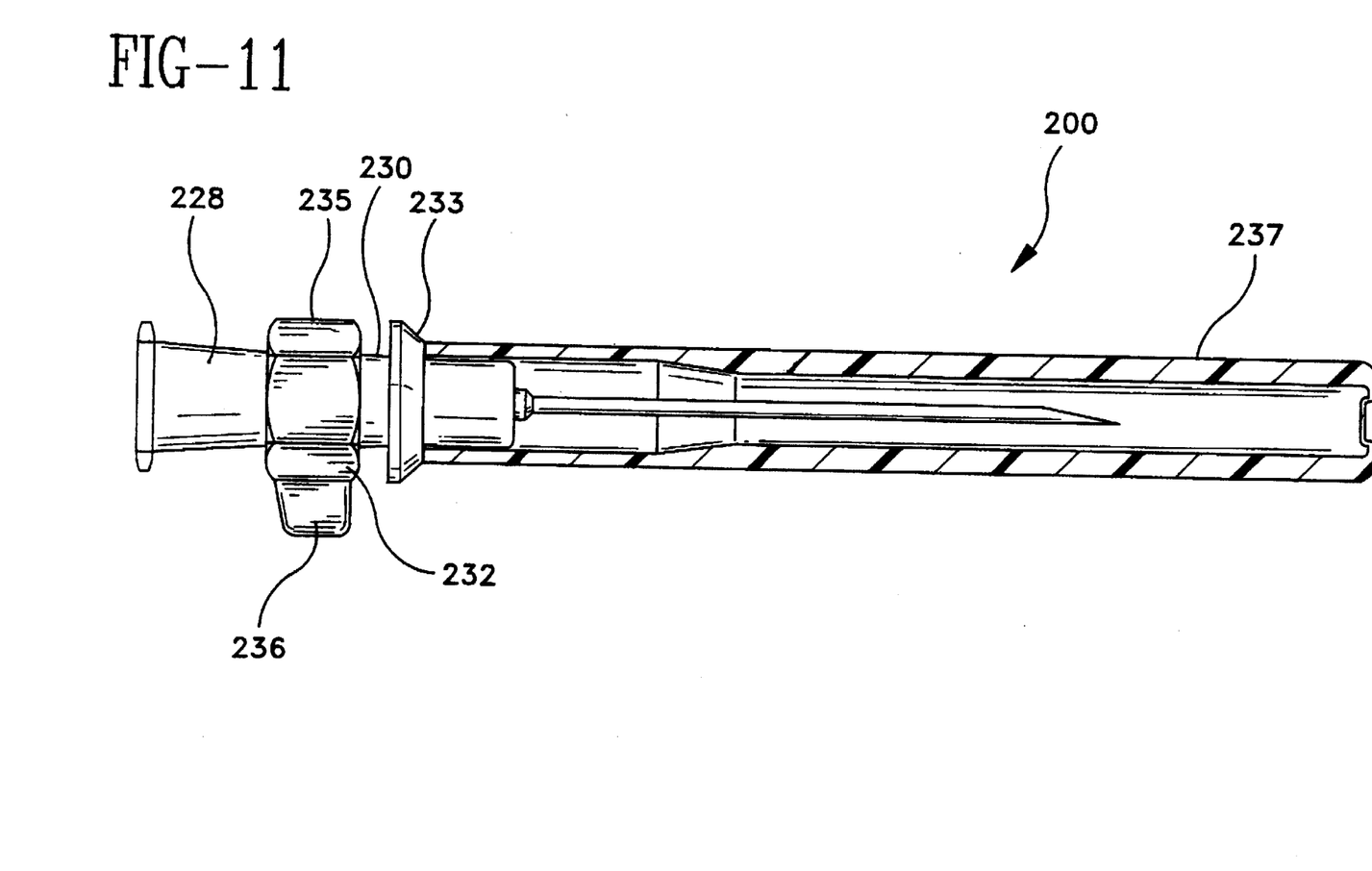
FIG. 11 is a side elevation view of an alternative needle shield assembly of the present invention illustrated without the collar and needle shield.

FIG. 11 illustrates an alternative needle shield assembly 200 of the present invention illustrated without the collar and needle shield. In this alternative embodiment a base member 230 is integrally molded and is part of a hub 228. Hub 228 further includes an enlarged portion 235 to facilitate removal and installation of the needle assembly. Because the collar is rotatably connected to the hub it may be difficult to install and remove the hub from a hypodermic syringe because rotation of the assembly will cause the shield and its connected collar to rotate around hub 228. The enlarged surface 235 provides a surface to grab to facilitate the removal and installation of the needle shield assembly. In this embodiment, enlarged portion 235 has an octagonal shape to further increase its utility as a gripping surface. In addition, hub 228 includes radially outwardly projecting tab 236 which further acts as an enhanced point of contact for connecting and disconnecting the needle shield assembly from a hypodermic syringe or similar device. Ways to facilitate the installation of the needle shield assembly of the present invention include providing structure on the hub which engages the rotatable shield when it is in the closed or intermediate position. Also, ribs can be provided on needle cover 37 to facilitate rotation of the cover which in turn rotates the hub. Also, side walls 50 and 51 of the needle shield can be designed to be flexible enough so that hand applied squeezing forces applied to the needle shield while it is in its intermediate position will cause the shield side walls to collapse and grab needle cover 37 so that torque may be transmitted through the needle shield, through the needle cover to the hub. Likewise, the needle shield sidewalls can be designed to grab the hub when the needle shield is in the closed position. Accordingly, the present invention provides means for applying torque to the hub to facilitate installation and removal of a needle shield assembly from a hypodermic syringe or similar device. Means for applying torque include alternative accessible hub structures including those with enlarged portions, such as enlarged portion 235 and/or radially projecting tabs, such as radially projecting tab 236. Means for applying torque can also include structure for engaging the needle cover and the needle shield, when the needle cover is in the intermediate position and providing flexible side walls on the needle shield so that digital force will deflect the side walls causing the needle shield to grab the needle cover for transmitting torque through the cover to the hub. Means for applying torque can also include structure for engaging the needle shield and the hub, when the needle shield is in the closed position, by providing flexible sidewalls on the needle shield so that digital force will deflect the sidewalls causing the needle shield to grab the hub for transmitting torque through the hub. Also, the structure for engaging the needle shield and the hub may be sufficiently strong that, in certain configurations, a flexible sidewall will not be necessary to apply torque from the needle shield to the needle hub. Structure on the needle shield for engaging the hub may include a series of inwardly projecting ledges, preferably having serrated or otherwise roughened distal ends, for contacting the hub and applying sufficient frictional force so that rotational force applied to the shield is transferred efficiently to the hub.

Hub 228 includes proximal raised portion 232 and distal raised portion 233. In this embodiment, distal raised portion 233 has a chamfered surface so that the collar (not shown) may be easily installed over needle cover 237 and into recess 234 by sliding the collar over the needle shield, forcibly past the chamfered distal raised portion 233 into recess 234.

Figure 12:
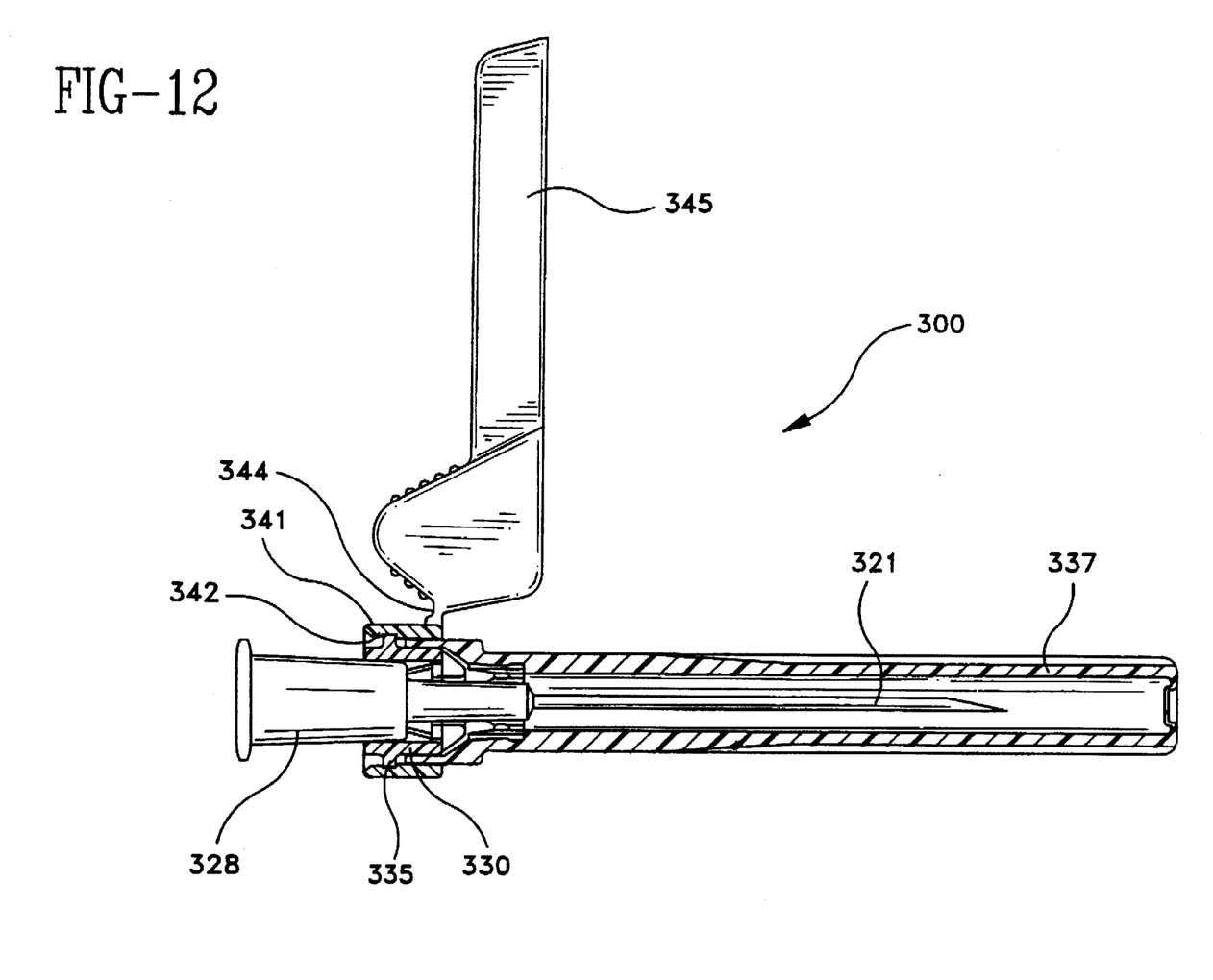
FIG. 12 is another alternative embodiment of the present needle shield assembly.

FIG. 12 illustrates another alternative needle shield assembly of the present invention. This alternative needle shield assembly functions similarly to the needle shield assembly of FIGS. 1–8. Alternative needle shield assembly 300, like the needle shield assembly of FIGS. 1–8, includes a needle cannula 321, a hub 328 which includes a base member 330, a needle cover 337 and collar 341 rotationally connected to the hub so that the collar can be rotated around the hub. An elongate needle shield 345 is pivotably connected to collar 341 through hinge 344. It is within the purview of present embodiment that the base member can be a separate element attached to the hub using methods described hereinabove or integrally formed as part of the hub. Rather than having a collar receiving recess the hub, the present embodiment has an annular flange 335. The rotational connection between collar 341 and hub 328 is affected by engagement of annular flange 335 with annular recess 336 inside collar 341.

One of the important features of the present invention is that the needle shield and collar can be assembled to the hub after the needle cover has been installed, thereby eliminating any potential for damaging the sharp needle tip during installation of the collar and needle shield assembly. One way to manufacture the needle shield assembly of the present invention is to attach base member 330 to hub 328 using one of the many manufacturing processes described hereinabove. The needle cannula is then assembled to the hub using a variety of known methods for securing the proximal end of the needle cannula to the distal end of the hub with epoxy adhesive being preferred. The needle assembly comprising the hub which includes the base member, integrally formed or separately attached, and the needle cannula is then assembled to the removable needle cover. At this point in the process, there exists a covered needle assembly wherein the needle cannula is protected from damage and its cleanliness is maintained by the needle cover. The needle assembly may be sterilized before further assembly into a finished product, or the collar may be joined to the needle hub by advancing the collar over the distal end of the needle cover, proximally until annular flange 335 contacts chamfered surface 342 on the collar. The chamfered surface is provided to allow the annular flange to spread the collar slightly so that annular flange 335 can snap into annular recess 336 in the collar. The needle shield may now be pivoted to its intermediate position described hereinabove, and packaged and sterilized or attached to a hypodermic syringe and packaged and sterilized. Sterilization may be accomplished by gas sterilization such as ETO or radiation sterilization. When using gas sterilization the package can be made of one hundred percent breathable material or at least have one surface of breathable material such as a blister package with a peelable, breathable top. The breathable surface is necessary to carry out the gas sterilization process. In radiation sterilization such breathable components can be used but are not necessary. Preferably, a quantity of packaged needle shield assemblies or packaged needle shield assemblies attached to devices such as a syringe are placed in a corrugated shipper and sealed before the sterilization process.

Figure 13:
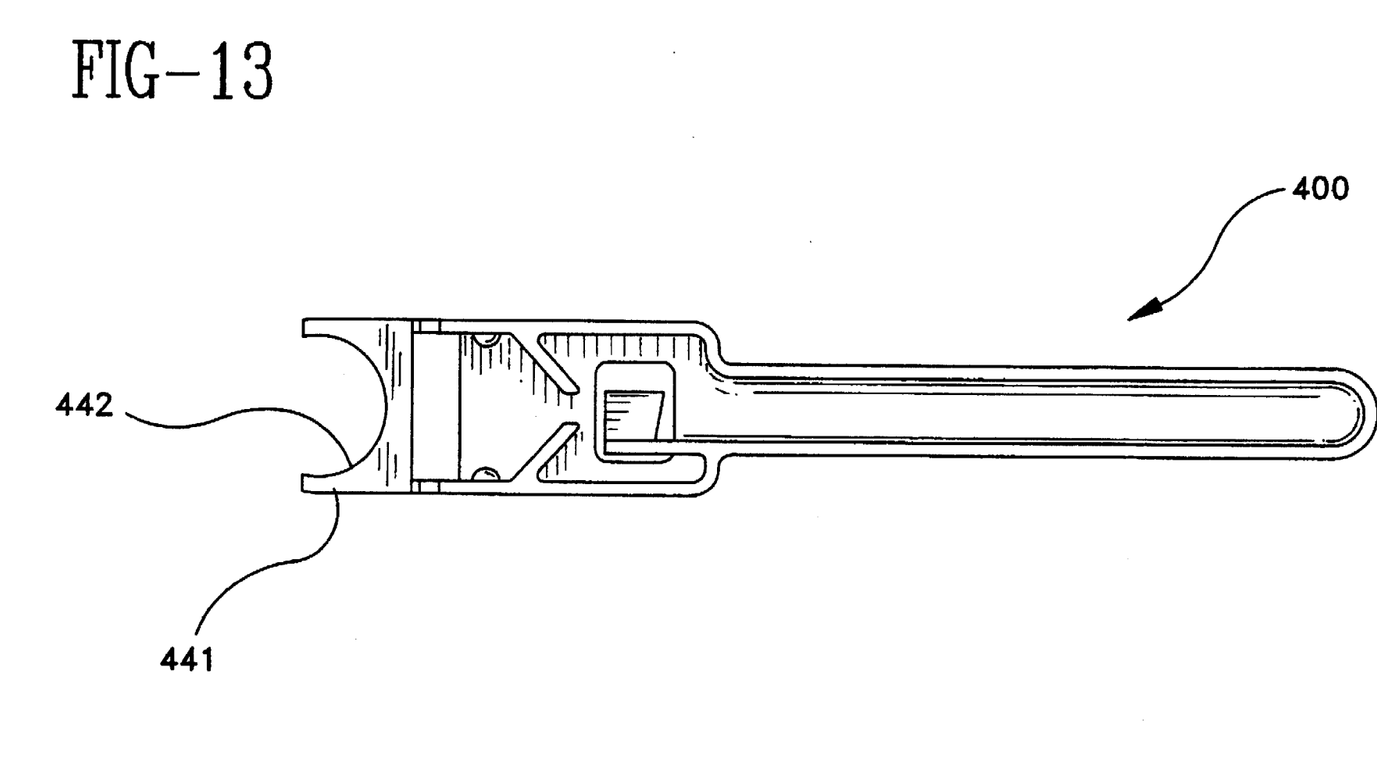
FIG. 13 illustrates an alternative needle shield and collar assembly.

It should be noted that throughout the specification the collar has been described as having an aperture of 360° in duration. It is within the purview of the present invention to have an aperture less than 360° and greater than 180° in duration which will be sufficient for the collar to be rotationally attached to a hub. FIG. 13 illustrates an alternative collar and needle shield assembly 400 which functions substantially identically to the embodiment of FIGS. 1–8. However, in this embodiment, collar 441 is semi-circular shaped having an aperture 442 of less than 360° and greater than 180° in duration. Collar 441 can be assembled axially over the needle cover and onto the needle hub using methods described hereinabove. Also, it may be assembled by moving said collar horizontally toward said hub and snapping the aperture over the appropriate structure on the needle hub. In either case the alternative needle shield and collar 400 maintains the important advantage of the present invention that collar and needle shield may be assembled to the needle hub after the needle cannula and needle cover have been installed.

It can be seen that the present invention provides a self-contained needle shield assembly and a method of making wherein the needle shield can be positioned in the needle shielding position using a one-handed procedure and the needle shield automatically locks in the needle shielding position so that the needle is unable to be reused. The needle shield assembly of the present invention also provides structure to protect the cleanliness of the needle until the needle is first used. The present invention also provides a self-contained needle shield assembly which allows the needle to be used twice, once for withdrawing medication into a syringe and then for injecting medication into a patient, while providing means for preventing the permanent locking of the needle shield until the final use by preventing the needle shield from being pivoted into the closed position while the needle cover is installed. The present invention also provides the advantage that the needle shield can be rotated with respect to the needle hub so that the needle shield can be oriented with respect to a needle cannula which has a sharpened beveled tip having a beveled surface. The advantage being that the needle shield can be rotated to the same side as the needle assembly as the bevel surface faces, making it easier to pierce a patient's vein without experiencing interference from the needle shield. Finally, the present invention provides the advantage of not having intermediate elements separating the needle hub from the fluid handling device, such as a syringe, which can waste medication by lengthening the fluid path, and making the entire assembly longer and possibly more difficult to use.

What is claimed is:

1. A method of making a needle shield assembly comprising the steps of:
   (a) providing a needle shield and collar assembly comprising a collar having an aperture therethrough of at least 180° duration and an elongate needle shield having a distal end and a proximal end hingedly connected to said collar, said needle shield including two sidewalls defining a longitudinal opening;
   (b) providing a needle cannula having a proximal end, a distal end and a lumen therethrough;
   (c) providing a hub having a proximal end for connecting to a fluid transfer device and a distal end for connecting to the proximal end of said needle cannula;
   (d) providing a base member having collar retaining portion configured to accept said collar through its aperture;
   (e) providing a rigid elongate needle cover having a distal end, an open proximal end and a sidewall therebetween defining a cavity;
   (f) attaching said base member to said hub;
   (g) attaching said proximal end of needle cannula to said hub;
   (h) placing said needle cover over said needle cannula and advance said needle cover until said proximal end of said needle cover removably engages said hub;
   (i) connecting said collar to said needle hub by advancing said collar axially over said needle cover toward said hub until said collar engages said collar retaining portion of said base member, said collar and needle shield assembly being oriented with said hub so that when said needle cover is removed from said needle hub, said collar is capable of pivoting from an open position where said needle cannula is exposed, to a closed needle protecting position where said needle cannula is within said longitudinal opening of said needle shield.

2. The method of making a needle shield assembly of claim 1 further including the steps of:
   (j) placing said needle shield assembly in a sterilizable package;
   (k) sealing said package;
   (l) sterilizing said needle shield assembly in said package.

3. The method of making the needle shield assembly of claim 1 deleting steps (d) and (f) and changing step (c) to:
   (c) providing a hub having a proximal end for connecting to a fluid transfer device and a distal end for connecting to the proximal end of said needle cannula, said hub further including a base member including a collar retention portion configured to accept said collar through its aperture.

4. The method of making a needle shield assembly of claim 1 wherein said distal end of said needle cannula includes a beveled surface further including the step of
   (j) rotating said collar with respect to said hub until said needle shield is on the same side of said hub as said bevel faces.

5. The method of making a needle shield assembly of claim 1 further including the steps of
   (j) providing a hypodermic syringe barrel having a distal end, a proximal end, and a circular side wall defining a chamber, said syringe barrel including a frusto-conically shaped tip having a passageway in fluid communication with said chamber;
   (k) engaging said proximal end of said needle hub and said tip of said syringe barrel so that said lumen of said needle cannula is in fluid communication with said chamber.

6. The method of making a needle shield assembly of claim 5 further comprising the steps of:
   (l) placing said syringe and needle shield assembly in a sterilizable package;
   (m) sealing said package; and
   (n) sterilizing said needle shield assembly and said syringe in said package.

7. The method of making a needle shield assembly of claim 1 changing step (i) to:
   (i) connecting said collar to said needle hub by advancing said collar horizontally toward said hub until said collar engages said collar retaining portion of said base member, said collar and said needle shield assembly being oriented with said hub so that when said needle cover is removed from said needle hub, said collar is capable of pivoting from an open position where said needle cannula is exposed, to a closed needle protecting position where said needle cannula is within said longitudinal opening of said needle shield.

* * * * *